United States Patent [19]

Babiarz et al.

[11] Patent Number: 5,492,954
[45] Date of Patent: Feb. 20, 1996

[54] SUBSTITUTED 1,4-DIAMINO-2-BUTENE STABILIZERS AND STABILIZED COMPOSITIONS

[75] Inventors: Joseph E. Babiarz, Amawalk, N.Y.; Glen T. Cunkle, Stamford, Conn.; Werner Rutsch, Fribourg, Switzerland

[73] Assignee: Ciba-Geigy Corporation, Tarrytown, N.Y.

[21] Appl. No.: 341,719

[22] Filed: Nov. 18, 1994

Related U.S. Application Data

[62] Division of Ser. No. 146,377, Nov. 1, 1993, Pat. No. 5,391,808, which is a division of Ser. No. 701,268, May 16, 1991, Pat. No. 5,283,367, which is a continuation-in-part of Ser. No. 400,649, Aug. 30, 1989, abandoned.

[51] Int. Cl.$^6$ .................................................. C10M 133/12
[52] U.S. Cl. ........................ 524/241; 524/242; 524/243; 524/246; 524/252; 524/254; 524/255
[58] Field of Search ..................................... 524/241, 242, 524/243, 246, 252, 254, 255

[56] References Cited

U.S. PATENT DOCUMENTS

| | | | |
|---|---|---|---|
| 2,419,735 | 9/1941 | Sloan | 252/40 |
| 3,098,841 | 7/1963 | Morris et al. | 260/45.9 |
| 3,461,165 | 8/1969 | Frye | 260/571 |
| 3,522,620 | 8/1970 | Nozawa et al. | 15/250.36 |
| 3,660,290 | 5/1972 | Schlobohm | 252/51.5 |
| 3,944,492 | 3/1976 | Wheeler | 252/50 |
| 4,180,084 | 12/1979 | Wegmuller et al. | 132/7 |
| 4,562,249 | 12/1985 | Schwander et al. | 531/641 |

FOREIGN PATENT DOCUMENTS

| | | |
|---|---|---|
| 417036 | 3/1991 | European Pat. Off. . |
| 1296478 | 5/1962 | France . |
| 2657582 | 7/1977 | Germany . |
| 2819005 | 11/1978 | Germany . |
| 606191 | 10/1978 | Switzerland . |
| 1092204 | 11/1967 | United Kingdom . |
| 1309845 | 3/1973 | United Kingdom . |
| 1438482 | 6/1976 | United Kingdom . |
| 1546809 | 5/1979 | United Kingdom . |

OTHER PUBLICATIONS

Fine Chemicals Patents Journal 6 (10) French 5:4 (Abstr. FR 1,427,290 (1965).
Derwent Abst. of JP 2228395 (1989).
Research Disclosure 15653 (Apr. 1977).
Yanigawa et al. Tetrahedron Letters, vol. 23, No. 52 (1982) pp. 5549–5552.
Horn et al. Chemical Absts, vol. 87 (1977) 119188d.
Horn et al. Chemical Absts. vol. 90 (1979) 109796y.
Horn, et al. Chem. Absts; vol. 90 (1979) 127533q.

*Primary Examiner*—Richard L. Raymond
*Attorney, Agent, or Firm*—Luther A. R. Hall

[57] ABSTRACT

N,N,N',N'-Tetrasubstituted 1,4-diamino-2-butenes where the substituents are alkyl, cycloalkyl, aralkyl, aryl or mixtures thereof provide effective antioxidant protection to lubricants and/or synthetic polymers.

17 Claims, No Drawings

SUBSTITUTED 1,4-DIAMINO-2-BUTENE STABILIZERS AND STABILIZED COMPOSITIONS

This is a divisional of application Ser. No. 08/146,377, filed on Nov. 1, 1993, now U.S. Patent No. 5,391,808, issued on Feb. 21, 1995, which is a divisional of application Ser. No. 07/701,268, filed on May 16, 1991, now U.S. Pat. No. 5,283,367, issued on Feb. 1, 1994, which is a continuation-in-part of application Ser. No. 07/400,649, filed on Aug. 30, 1989, now abandoned.

N,N,N',N'-Tetrasubstituted 1,4-diamino-2-butenes where the substituents are alkyl, cycloalkyl, aralkyl, aryl or mixtures thereof provide effective antioxidant protection to lubricants and/or synthetic polymers.

BACKGROUND OF THE INVENTION

The instant substituted 1,4-diamino-2-butene compounds fall into three general groups depending on the various substituents on the two N-atoms.

When said substituents are alkyl, compounds having at least one lower alkyl, preferably two lower alkyl groups, on each N-atom are known. Lower alkyl includes methyl, ethyl, propyl butyl and amyl. Typical is N,N,N',N'-tetramethyl-2-butene-1,4-diamine. The use of such lower alkyl compounds as stabilizers is not disclosed. The instant alkyl substituents are higher alkyls such as octyl, decyl, octadecyl and the like.

When said substituents are aralkyl, the hydrochloride salt of such the tetrabenzyl compound has a GAS number (5443-70-9), but no other published reference is known for said material nor is there any known utility for said compound. The other tetra-aralkyl compounds are believed to be novel materials. The stabilized compositions where the stabilizers are the instant compounds having one or more aralkyl substituents are not disclosed in the prior art.

When said substituents are aryl, British Patent No. 1,438,482 generically describes lubricant compositions containing substituted aryl mines of the formula R—X where R is a secondary amine residue containing two aromatic groups attached to nitrogen such as $(Ar)_2N$—. This reference also generically describes compounds of the formula R—Y—R where Y is inter alia —$CH_2CH=CHCH_2$—. The only such compounds specifically disclosed by the British reference are those where R is an alkylated phenothiazine moiety. The closest compound of this reference is 1,4-but-2-ene-bis(3,7-dioctylphenothiazine).

British Patent No. 1,438,482 does not disclose or suggest that the compounds described therein can provide effective antioxidant protection to synthetic polymer compositions.

OBJECTS OF THE INVENTION

On object of this invention is to provide new N,N,N',N'-tetrasubstituted 1,4-diamino-2-butene compounds which are useful stabilizers for various substrates.

Another object of this invention is to provide synthetic polymer compositions stabilized by incorporating therein an effective stabilizing amount of an instant compound.

Still another object of the invention is to provide a lubricant composition stabilized by incorporating therein an effective stabilizing amount of an instant compound.

DETAILED DISCLOSURE

The instant invention pertains to a composition stabilized against the deleterious effects of heat or oxygen which comprises (a) a synthetic polymer or a lubricant, and
(b) an effective stabilizing mount of a compound of formula I, II or III

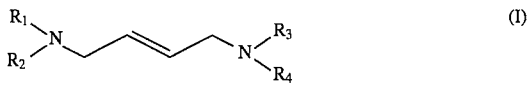

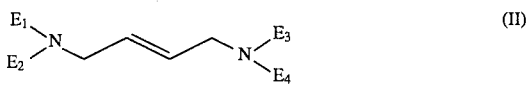

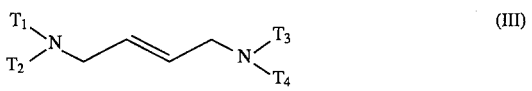

wherein $R_1$, $R_2$, $R_3$ and $R_4$ are independently a linear or branched alkyl of 8 to 30 carbon atoms; alkyl of 1 to 20 carbon atoms substituted with cycloalkyl of 5 to 12 carbon atoms; or alkyl of 1 to 20 carbon atoms terminated with —$OR_5$, —$NR_6R_7$, —$SR_8$, —$COOR_9$ or —$CONR_{10}R_{11}$, where $R_5$, $R_6$, $R_7$, $R_8$ and $R_9$ are independently alkyl of 1 to 20 carbon atoms or alkenyl of 3 to 18 carbon atoms, and $R_{10}$ and $R_{11}$ are independently hydrogen or the same meaning as Rs; or alkyl of 3 to 18 carbon atoms interrupted by one or more —O—, —S—, —SO—, —$SO_2$—, —CO—, —COO—, —OCO—, —$CONR_{12}$—, —$NR_{12}CO$— or —$NR_{13}$— where R12 and R13 have the same meaning as $R_{10}$; or $R_1$, $R_2$, $R_3$ and $R_4$ are independently cycloalkyl of 5 to 12 carbon atoms; or alkenyl of 3 to 20 carbon atoms;

$E_1$ is aralkyl of 7 to 15 carbon atoms or said aralkyl substituted on the aryl ring by one to three groups selected from alkyl of 1 to 12 carbon atoms, —CN, —$NO_2$, halogen, —$OR_5$, —$NR_6R_7$, —$SR_8$, —$COOR_9$ or —$CONR_{10}R_{11}$, where $R_5$, $R_6$, $R_7$, $R_8$, $R_9$, $R_{10}$ and $R_{11}$ are as defined above, $E_2$, $E_3$ and $E_4$ are independently a linear or branched alkyl of 1 to 30 carbon atoms; alkyl of 1 to 20 carbon atoms substituted with cycloalkyl of 5 to 12 carbon atoms; or alkyl of 1 to 20 carbon atoms terminated with —CN, —$OR_5$, —$NR_6R_7$, —$SR_8$, —$COOR_9$ or —$CONR_{10}R_{11}$, where $R_5$, $R_6$, $R_7$, $R_8$ and $R_9$ are independently alkyl of 1 to 20 carbon atoms or alkenyl of 3 to 18 carbon atoms, and $R_{10}$ and $R_{11}$ are independently hydrogen or the same meaning as $R_5$; or alkyl of 3 to 18 carbon atoms interrupted by one or more —O—, —S—, —SO—, —$SO_2$—, —CO—, —COO—, —OCO—, —$CONR_{12}$—, —$NR_{12}CO$— or —$NR_{13}$— where $R_{12}$ and $R_{13}$ have the same meaning as $R_{10}$; or $E_2$, $E_3$ and $E_4$ are independently cycloalkyl of 5 to 12 carbon atoms, alkenyl of 3 to 20 carbon atoms, aralkyl of 7 to 15 carbon atoms or said aralkyl substituted on the aryl ring by one to three groups selected from alkyl of 1 to 12 carbon atoms, —CN, —$NO_2$, halogen, —$OR_5$, —$NR_6R_7$, —$SR_8$, —$COOR_9$ or —$CONR_{10}R_{11}$, where $R_5$, $R_6$, $R_7$, $R_8$, $R_9$, $R_{10}$ and $R_{11}$ are as defined above, or aryl of 6 to 10 carbon atoms or said aryl substituted by one to three substituents selected from the group consisting of alkyl of 1 to 20 carbon atoms, cycloalkyl of 5 to 12 carbon atoms and aralkyl of 7 to 15 carbon atoms, and $T_1$, $T_2$, $T_3$ and $T_4$ are independently aryl of 6 to 10 carbon atoms or said aryl substituted by one to three substituents selected from the group consisting of alkyl of 1 to 20 carbon atoms, cycloalkyl of 5 to 12 carbon atoms and aralkyl of 7 to 15 carbon atoms.

Preferably $R_1$, $R_2$, $R_3$ and $R_4$ are independently cycloalkyl of 5 or 6 carbon atoms, a linear or branched alkyl of 8 to 20 carbon atoms or alkyl of 1 to 4 carbon atoms substituted with cycloalkyl of 5 or 6 carbon atoms.

Most preferably $R_1$, $R_2$, $R_3$ and $R_4$ are the same and are alkyl of 8 to 18 carbon atoms, cyclohexyl or cyclohexylmethyl.

Preferably $E_1$ is benzyl, benzyl substituted on the phenyl ring by alkyl of 1 to 8 carbon atoms, α-methylbenzyl or 1-naphthylmethyl.

Most preferably $E_1$ is benzyl or 1-naphthylmethyl.

Preferably $E_2$, $E_3$ and $E_4$ are independently alkyl of 1 to 20 carbon atoms, benzyl, benzyl substituted on the phenyl ring by alkyl of 1 to 8 carbon atoms or by methoxycarbonyl, phenyl, 1-naphthyl or said phenyl or said 1-naphthyl substituted by alkyl of 1 to 8 carbon atoms; cyclohexylmethyl or 2-cyanoethyl.

Most preferably $E_3$ has the same meaning as $E_1$ and is benzyl or 1-naphthylmethyl; and $E_2$ and $E_4$ are alkyl of 1 to 20 carbon atoms, benzyl or 1-naphthylmethyl.

Preferably $T_1$, $T_2$, $T_3$ and $T_4$ are independently phenyl, 1-naphthyl or said phenyl or said 1-naphthyl substituted by alkyl of 1 to 8 carbon atoms.

Most preferably $T_1$ and $T_3$ are phenyl, and $T_2$ and $T_4$ are phenyl or 1-naphthyl. Especially preferably, $T_1$, $T_2$, $T_3$ and $T_4$ are each phenyl.

The compounds of formula I and formula II are conveniently prepared by reacting an appropriate secondary amine with 2-butene-1,4-diol diacetate in the presence of a catalyst such as tetrakis(triphenylphosphine)palladium(0) in an organic solvent such as tetrahydrofuran.

The compounds of formula III are conveniently prepared by the reaction of the appropriate secondary diarylamine with 1,4-dibromobut-2-ene in the presence of an aqueous mixture of potassium iodide, a phase transfer catalyst and alkali.

The starting materials for making the instant compounds are largely items of commerce.

When any of the aforementioned groups of $R_1$ to $T_4$ are alkyl, they are, for example, methyl, ethyl, isopropyl, n-butyl, sec-butyl, tert-butyl, isoamyl, tert-amyl, n-hexyl, 2-ethylhexyl, isooctyl, n-octyl, tert-octyl, nonyl, decyl undecyl, lauryl, tridecyl, tetradecyl, hexadecyl, heptadecyl, octadecyl, eicosyl, tricontyl and branched isomers thereof.

Cycloalkyl of 5 to 12 carbon atoms includes, for example, cyclopentyl, cyclohexyl, cycloheptyl, cyclooctyl and cyclododecyl.

Phenylalkyl of 7 to 9 carbon atoms includes, for example, benzyl, phenethyl, α-methylbenzyl and α,α-dimethylbenzyl.

Aryl of 6 to 10 carbon atoms includes, for example, phenyl, 1-naphthyl and 2-naphthyl.

Aryl or phenylalkyl substituted by alkyl is, for example, tolyl, xylyl, ethylphenyl, 4-methylbenzyl, tert-butylphenyl, tert-octylphenyl, tert-dodecylphenyl, nonylnaphthyl or tert-octylnaphthyl.

The compositions where component (a) is a synthetic polymer are especially a part of this invention, most particularly when the synthetic polymer is a polyolefin such as polypropylene or is an elastomer such as dynamically crosslinked polypropylene/nitrile rubber.

The instant compounds are effective stabilizers for synthetic polymers subject to the deleterious effects of heat and/or oxygen especially during processing at elevated temperatures.

Still another part of this invention, especially where the substituent groups on the N-atoms are aryl or phenylalkyl, are compositions where component (a) is an industrial lubricant such as lubricating oils, turbine oils, transformer oils, transmission fluids, glass-annealing oils, greases, steam turbine oils, gasoline engine oils, diesel engine oils, jet engine oils, metal working fluids and the like. They are also effective in stabilizing waxes, heating oil, bunker and residual oils, asphalt, gasoline and jet engine fuel.

Still another aspect of the instant invention are the novel compounds of formula I or formula II

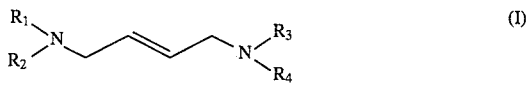

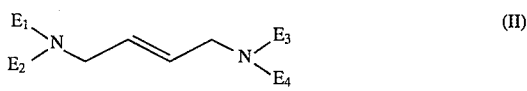

wherein $R_1$, $R_2$, $R_3$ and $R_4$; and $E_1$, $E_2$, $E_3$ and $E_4$ are as defined above; with the proviso that $E_1$, $E_2$, $E_3$ and $E_4$ are not all benzyl at the same time.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/ vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example, 2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol 2,6-di-tert-butyl-4-methoxymethylphenol 1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example, 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl—N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1.2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3', 5'-bis-(α,α-dimethylbenzyl), 3'-tert-butyl-5'-(2-(omega-hydroxy-octa-(ethylencoxy)carbonylethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2', 4'-trihydroxy-and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'-(1,2-ethanediyl)-bis-(3,3,5,5-tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino, 1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4- tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl )-amino-s-triazin-2-yl]-1,10-diamino-4,7-diazadecane, mixed [2,2,6,6-tetramethylpiperidin-4-yl/lβ,β,β',β'-tetramethyl-3,9-(2,4,8,10-tetraoxaspiro[5.5]undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl)sebacate.

A most preferred hindered amine compound is bis(2,2,6,6-tetramethylpiperidin-4-yl)sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]1,10-diamino-4,7-diazadecane or bis(1-octyloxy-2,2,6,6-tetramethylpiperidin-4-yl)sebacate.

The lubricant of component (a) is particularly a lubricating oil or grease wherein the base medium is a hydrocarbon or synthetic lubricant. The preferred base fluids of this invention include the hydrocarbon mineral oils, olefin fluids, polyolefin fluids, polyether fluids, polyacetals, alkylene oxide polymers, silicone-base fluids and ester fluids. The esters of dicarboxylic acids and monohydric alcohols and the trimethylolpropane and pentaerythritol esters of monocarboxylic acids are particularly of interest. Suitable diesters include the esters of oxalic, malonic, succinic, glutaric, adipic, pimelic, suberic, azelaic and sebacic acids, cyclohexane dicarboxylic acid, phthalic acid, terephthalic acid and the like; and alcohols having 1 to 20 carbon atoms. A commonly used diester is di(2-ethylhexyl) sebacate.

The acids used in forming the trimethylolpropane and pentaerythritol esters include those containing 1 to 30 carbon atoms having straight or branched chain aliphatic, cycloaliphatic, aromatic or alkylated aromatic structures. Mixtures of one or more of such acids may also be used in the preparation of these tri-and tetra-esters. Typical carboxylic acids include, acetic, propionic, butyric, valeric, isovaleric, caproic, caprylic, pelargonic, capric, isodecanoic, lauric, benzoic, nonylbenzoic, dodecylbenzoic, naphthoic, cyclohexanoic and the like. The acids most particularly preferred are pelargonic and commeric valeric acid which contains both n-valeric and isovaleric acids.

The most preferred ester used in this invention is an ester prepared from pentaerythritol, pelargonic, n-valeric and isovaleric acids.

The instant compounds are sufficiently soluble in lubricants to afford the desired antioxidant stabilizing effects. Suitable concentrations range from about 0.001% to about 10% by weight based on the total lubricant composition. Preferably the effective stabilizing amount of the instant compounds is from about 0.1% to about 5% by weight of the total lubricant composition.

The lubricant composition of the instant invention find a wide variety of end uses including engine oils, such as aviation engine oils, automotive engine oils, diesel engine oils, railroad diesel oils, truck diesel oils and the like.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent brightstocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tert-esters, complex esters and polyesters derived from carboxylic acid esters of formula: $G_1$-OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ monocarboxylic acids or mixtures thereof, whereas suitable tetraesters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemic, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants
1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methyl phenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acrylaminophenols 4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid with mono- or polyhydric alcohols, for example with methanol, diethyleneglycol, octadecanol, triethyleneglycol, 1,6-hexane-diol, pentaerythritol, neopentylglycol, tris-hydroxyethyl-isocyanurate, thiodiethyleneglycol, bis-hydroxyethyl-oxalic acid diamide.

8. Esters of β(5-tert-butyl-4-hydroxy-3-methylphenyl)-priopionic acid with mono-or polyhydric alcohols, for example with methanol, diethyleneglycol, octadecanol, triethyleneglycol, 1,6-hexane-diol, pentaerythritol, neopentylglycol, tris-hydroxyethyl-isocyanurate, thiodiethyleneglycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants: N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl—N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diamino-diphenyl-methane, N,N,N',N'-tetramethyl-4,4'-diamino-diphenylmethane, 1,2-di-(phenyl-amino)ethane, 1,2-di-[2-methyl-phenyl)-amino]-ethane, 1,3-di-(phenylamino)-propane, (o-tolyl)-biguanide, di-[4-1',3'-dimethylbutyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine.

Examples for other antioxidants: Aliphatic or aromatic phosphites, esters of thiodipropionic acid or of thiodiacetic acid, or salts of dithiocarbamic or dithiophosphoric acid.

Examples of metal passivators, for example for copper, are: Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

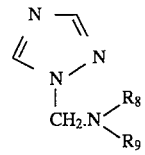

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and-anhydrides, e.g. dodecenyl-succinic acid anhydride, succinic acid partial esters and amines, 4-nonyl-phenoxy-acetic acid.

b) Nitrogen-containing compounds, e.g.
  I. Primary, secondary or tertiary aliphatic or cycloaliphatic amines and amine-salts of organic and inorganic acids, e.g. oil-soluble alkyl-ammonium carboxylates
  II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonyl-naphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula

in which $X_2$ is —O—, —S—, —$SO_2$—C(O)—O— or —N(Rd) in which $R_{12}$ is H or $C_1$–$C_{12}$alkyl, $R_{13}$ is unsubstituted $C_1$–$C_4$alkyl or $C_2$–$C_5$alkyl substituted by one to three hydroxyl groups, $R_{14}$ is hydrogen, unsubstituted $C_1$–$C_4$alkyl or $C_2$–$C_5$alkyl substituted by one to three hydroxyl groups provided that at least one of $R_{13}$ and $R_{14}$ is hydroxy-substituted, and $R_{12}$ is $C_2$–$C_{20}$alkyl —$CH_2$—CH(OH)—$CH_2NR_{13}R_{14}$ or $R_{12}$ is $C_2$–$C_{18}$alkenyl, $C_2$–$C_3$alkynyl or $C_5$–$C_{12}$cycloalyl provided that, when $X_2$ is —O— or —C(O)—O—, $R_{12}$ is branched $C_4$–$C_{20}$alkyl. These compounds are described in GB Patent Specification 2172284A.

h) Compounds having the formula:

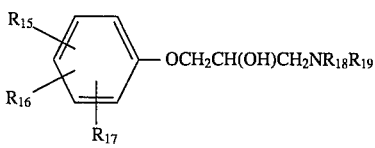

in which $R_{15}$, $R_{16}$, $R_{17}$ are, independently, hydrogen, $C_1$–$C_{15}$alkyl, $C_5$–$C_{12}$cycloalkyl, $C_6$–$C_{15}$aryl or $C_7$–$C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are: Polyacrylates, polymethacrylates, vinylpyrrolidone/methacrylate-co-polymers, polyvinylpyrrolidones, polybutanes, olefin-co-polymers, styrene/-acrylate-copolymers, polyethers.

Examples of pour-point depressants are: Polymethacrylates, alkylated naphthalene derivatives.

Examples of dispersants/detergents are: Polybutenylsuccinic acid-amides or imides, polybutenyl-phosphonic acid derivatives, basic magnesium-, calcium-, and bariumsulfonates and -phenolates.

Examples of anti-wear additives and extreme pressure additives are: Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are presented for the purpose of illustration only and are not to be construed to limit the nature or scope of the instant invention in any manner whatsoever.

EXAMPLE 1

N,N,N',N'-Tetradecyl-2-butene-1,4-diamine

A solution of di-n-decylamine (10.9 g, 36.6 mmol) and 2-butene-1,4-diol diacetate (3.15 g, 18.3 mmol) in tetrahydrofuran (THF) (150 ml) is treated with tetrakis(triphenylphosphine)palladium(0) (1.0 g, 0.9 mmol) and stirred at room temperature overnight. The reaction mixture is concentrated in vacuo to a oil that is redissolved in THF (500 ml) and treated with 20% aqueous sodium hydroxide (250 ml). The mixture is stirred for one hour, concentrated, and extracted with ether. The ether extracts are dried and concentrated giving an orange oil which is purified by medium pressure chromatography (silica gel; 25% ethyl acetate in hexanes). The title compound is isolated as 5.8g (49% yield) of a clear oil.

Analysis: Calcd for $C_{44}H_{90}N_2$: C, 81.6; H, 14.0; N, 4.3. Found: C, 81.4; H, 14.2; N, 4.7.

EXAMPLE 2

N,N,N',N'-Tetracyclohexylmethyl-2-butene-1,4-diamine

A solution of dicyclohexylmethylamine (13.3 g, 63.6 mmol) and 2-butene-1,4-diol diacetate (5.45 g, 31.8 mmol) in THF (100 ml) is treated with tetrakis(triphenylphosphine)palladium(0) (1.0 g, 0.9 mmol) and stirred at room temperature overnight. The reaction mixture is concentrated in vacuo to a solid that is redissolved in THF (500 ml) and treated with 20% aqueous sodium hydroxide (250 ml). The mixture is stirred for one hour, concentrated, and extracted with ether. The ether extracts are dried and concentrated giving an orange solid which is purified by crystallization from isopropyl alcohol. The title compound is isolated as a white solid in a yield of 10.7g (71%): mp 72°–73° C.

Analysis: Calcd for $C_{32}H_{58}N_2$: C, 81.6; H, 12.4; N, 6.0. Found: C, 81.8; H, 12.7; N, 5.8.

EXAMPLE 3

N,N,N',N'-Tetracyclohexyl-2-butene-1,4-diamine

A solution of dicyclohexylamine (20.4 g, 0.11 mol) and 2-butene-1,4-diol diacetate (9.6 g, 0.056 mol) in THF (100 ml) is treated with tetrakis(triphenylphosphine)palladium (0) (1.0 g, 0.9 mmol) and stirred at room temperature overnight. The reaction mixture is concentrated in vacuo to a solid that is redissolved in THF (500 ml) and treated with 20% aqueous sodium hydroxide (250 ml). The mixture is stirred for one hour, concentrated, and extracted with ether. The ether extracts are dried and concentrated giving an orange solid which is purified by crystallization from isopropyl alcohol. The title compound is isolated as a while solid in a yield of 4.8g (21%): mp 136°–138° C.

Analysis: Calcd for $C_{28}H_{50}N_2$: C, 81.1; H, 12.2; N, 6.8. Found C, 80.8; H, 12.7; N, 6.7

EXAMPLE 4

N,N,N',N'-Tetrabenzyl-2-butene-1,4-diamine

A solution of dibenzylamine (13.0 g, 66 mmol) and 2-butene-1,4-diol diacetate (4.0 g, 33 mmol) in 50 ml of tetrahydrofuran (THF) is treated with tetrakis(triphenylphosphine)palladium(0) (1.0 g, 0.9 mmol) and stirred at room temperature overnight. The reaction mixture is concentrated in vacuo to a solid that is redissolved in THF (100 ml) and treated with 20% aqueous sodium hydroxide (25 ml). The mixture is stirred for one hour, then concentrated and extrated with diethyl ether. The ether extracts are dried and concentrated to give 6.9 g (47% yield) of the title compound as a white solid melting at 114°–115° C.

Analysis: Calcd for $C_{32}H_{34}N_2$: C, 86.1; H, 7.7; N, 6.3. Found: C, 86.1; H, 7.7; N, 6.2.

EXAMPLE 5

N,N,N',N'-Tetraphenyl-2-butene-1,4-diamine

A vigorously stirred mixture of diphenylamine (150 g, 0.9 mol), 1,4-dibromobut-2-ene (104 g, 0.49 mol), potassium iodide (8 g, 0.05 mol), tetrabutylammonium bromide (7 g, 0.025 mol), sodium hydroxide (43 g, 1.06 mol) and 150 ml of water is warmed to 60° C. for five hours. The mixture is allowed to cool to room temperature. The solids formed are collected and washed with water. The residue is recrystallized from ethanol to give 69 grams (36% yield) of the title compound as a tan solid melting at 105°–107° C.

Analysis: Calcd for $C_{28}H_{26}N_2$: C, 86.1; H. 6.7; N, 7.2. Found: C, 85.8; H, 6.5; N, 7.2.

EXAMPLE 6

N,N'-Diphenyl-N,N'-di-1-naphthyl-2-butene-1,4-diamine

A mixture of N-phenyl-1-naphthylamine (63 g, 0.29 mol) and 1.4-dibromobut-2-ene (12 g, 0.056 mol) is heated to 70° C. for three days. The resulting reaction mass is allowed to cool and is then extracted with 3×100 ml of hot hexane. The combined hexane extracts are concentrated in vacuo to an oil which is chromatographed (silica gel. 95/5 cyclohexane/diethyl ether) to give an oil. Said oil is then crystallized from ether to give 4.8 g (17.5% yield) of the title compound as a tan solid melting at 140°–142° C.

EXAMPLE 7

N,N'-Dibenzyl-N,N'-di-α-methylbenzyl-2-butene-1,4-diamine

The procedure of Example 4 is repeated with N-benzyl-α-methylbenzylamine prepared by the method of M. Brook et al., Synth. Comm. 18, 893 (1988). The title compound is obtained in a 20% yield after recrystallization from isopropanol as a white solid melting at 131°–134° C.

Analysis: Calcd for $C_{34}H_{38}N_2$: C, 86.0; H, 8.1; N, 5.9. Found: C, 85.1; H, 8.2; N, 5.7.

EXAMPLE 8

N,N'-Dicyclohexylmethyl-N,N'-dibenzyl-2-butene-1,4-diamine

The general procedure of Example 4 is repeated with N-cyclohexylmethyl-N-benzylamine prepared by the method of S. C. Shim et al., Tetrahedron Letters 31, 105 (1990). After crystallization from isopropanol, the title compound is obtain in an 82% yield as a white solid melting at 92°–93° C.

Analysis: Calcd for $C_{32}H_{46}N_2$: C, 83.8; H, 10.1; N, 6.1. Found: C, 83.9; H, 10.3; N, 6.1.

EXAMPLE 9

N,N'-Dibenzyl-N,N'-di-2-cyanoethyl-2-butene-1,4-diamine

Following the general procedure of Example 4 using 3-(benzylamino)propionitrile and after purification of the crude product by chromatography, the title compound is obtained as a clear oil in a yield of 65%.

Analysis: Calcd for $C_{24}H_{28}N_4$: C, 77.4; H, 7.6; N, 15.1. Found: C, 76.9; H, 7.5; N, 15.1.

EXAMPLE 10

N,N'-Di-1-naphthylmethyl-N,N'-dibenzyl-2-butene-1,4-diamine

The general procedure of Example 4 is repeated with N-1-naphthylmethyl-N-benzylamine prepared by the method of Dahn et at., Helv. Chim. Acta. 37, 565 (1954). After crystallization from 30% ethyl acetate in isopropanol, the title compound is obtained in a yield of 35% as a white solid melting at 121°–122° C.

Analysis; Calcd for $C_{40}H_{38}N_2$: C, 87.9; H, 7.0; N, 5.1. Found: C, 87.5; H, 7.0; N, 5.0.

EXAMPLE 11

N,N-Dicyclohexylmethyl-N',N'-dibenzyl-2-butene-1,4-diamine

A solution of dibenzylamine (40 g, 0.2 mol) and 2-butene-1,4-diol diacetate (105 g, 0.61 mol) dissolved in 150 ml of tetrahydrofuran (THF) is treated with tetrakis(triphenylphosphine)palladium(0) (1.0 g, 0.9 mmol) and stirred at room temperature overnight. The reaction mixture is concentrated in vacuo and the excess 2-butene-1,4-diol diacetate is removed by bulb-to-bulb distillation at 80°–90° C./1 mm. The residue is purified by eluting through a short plug of silica gel (1:1 ethyl acetate:hexanes). 1-Acetoxy-4-dibenzylamino-2-butene is obtained in a yield of 59.2 g (95%).

A solution of 1-acetoxy-4-dibenzylamino-2-butene (10.1 g, 33 mmol) and dicyclohexylmethylamine (6.8 g, 32 mmol) in 50 ml of THF is treated with tetrakis(triphenylphosphine)palladium (0) (1.0 g, 0.9 mmol) and stirred at room temperature overnight. The reaction mixture is concentrated in vacuo to a solid which is redissolved in 100 ml of THF and treated with 25 ml of 20% aqueous sodium hydroxide. The mixture is stirred for one hour, concentrated and extracted with diethyl ether. The ether extracts are dried and concentrated to give a solid which is then purified by crystallization from isopropanol. The title compound is obtained in a yield of 9.7 g (65%) as a white solid melting at 61°–62° C.

Analysis: Calcd for $C_{32}H_{46}N_2$: C, 83.8; H, 10.1; N, 6.1. Found: C, 83.8; H, 10.2; N, 5.9.

EXAMPLE 12

N,N,N',N'-Tetra-p-methoxycarbonylbenzyl-2-butene-1,4-diamine

Di(p-carboxybenzyl)amine (17.2 g, 0.06 mol), prepared according to the method given in U.S. Pat. No. 3,335,176, is suspended in 300 ml of methanol. The suspension is then saturated with hydrogen chloride gas without cooling. The resulting mixture is then refluxed for five hours, cooled and finally concentrated to a solid. The solid is suspended in water, the aqueous suspension is then made basic using ammonium hydroxide and finally extracted with ethyl acetate. The organic extracts are dried over anhydrous magnesium sulfate and concentrated to give di(p-methoxycarbonylbenzyl)amine as an oil.

Di(p-methoxycarbonylbenzyl)amine (14.1 g, 0.045 mol) and 2-butene-1,4-diol diacetate (3.9 g, 0.023 mol) are dissolved in 150 ml of THF. Tetrakis(triphenylphosphine)palladium (0) (1.0 g, 0.9 mmol) is added and the resulting solution is stirred for three days at room temperature. The solution is concentrated, the residue redissolved in THF and treated with 20 ml of ammonium hydroxide solution, stirred for 15 minutes and finally concentrated to a solid which is washed with water, diethyl ether and dried. The title compound is obtained in a 72% yield as a white solid melting at 161°–163° C.

EXAMPLE 13

N,N,N',N'-Tetra-p-methoxybenzyl-2-butene-1,4-diamine

Following the general procedure of Example 4 by replacing dibenzylamine with an equivalent amount of di(p-methoxybenzyl)amine, prepared by the method of Tanaka et al., Chem. Pharm. Bull, 15, 774 (1067), the title compound is afforded in a 33% yield as a white solid melting at 128°–130° C.

EXAMPLE 14

N,N-Diphenyl-N',N'-dibenzyl-2-butene-1,4-diamine

Following the general procedure of Example 11 by replacing 1-acetoxy-4-dibenzylamino-2-butene with 1-acetoxy-4-diphenylamino-2-butene and replacing dicyclohexylmethylamine with dibenzylamine, the title compound is obtained as a white solid.

EXAMPLE 15

Process Stabilization of Dynamically Crosslinked Polypropylene/Nitrile Rubber

A Brabender cavity heated to 190° C. is charged with 55 g of a dynamically crosslinked polypropylene/nitrile rubber resin (GEOLAST, Monsanto). The resin is stirred under nitrogen for three minutes, 4% by weight of the stabilizer test compound is added and mixed under nitrogen for an additional seven minutes. The sample is removed, flattened in a cold press, and is subjected to the following procedure:
Compression Molding
Plaques [60 mil and 4"×4" (1.524 mm and 10.16 cm×10.16 cm)] are prepared by loading 18–20 g of said rubber per plaque. The temperature of the compression molding press platens is adjusted to 200° C. The resin is preheated to allow it to flow. The resin is compression molded at low pressure [2000 psi (140 Kg/cm$^2$)] for four minutes and at high pressure [50,000 psi (3500 Kg/cm$^2$)] for four minutes.
Sample Preparation and Oven Aging
The samples are cut on a Naef press using Die C whose dimensions are described in ASTM D412. The cut samples are mounted in replicates and oven aged at 135° C. for seven days before tensile testing for % retention of elongation according to ASTM D412. A greater % retention of elongation indicates a more effective stabilizer.

| Test Compound* of Example | % Retention of Elongation After 7 Days at 135° C. |
|---|---|
| Blank | 0 |
| AOI | 10 |
| Example 1 | 50 |
| Example 2 | 52 |
| Example 4 | 40 |
| Example 5 | 55 |
| Example 6 | 52 |
| Example 8 | 68 |
| Example 10 | 90 |
| Example 11 | 64 |
| Example 12 | 54 |
| Example 14 | 77 |

| Test Compound* of Example | % Retention of Elongation After 7 Days at 135° C. |
|---|---|

*AOI is the oligomeric condensation product of diphenylamine and acetone.

The instant compounds are clearly more effective as stabilizers than the prior art stabilizer in this crosslinked polypropylene/nitrile rubber.

EXAMPLE 16

Stabilization of Gasoline Engine Oils

The antioxidant effectiveness of the instant compounds in engine oils is measured by the Thin-Film Oxygen Uptake Test (TFOUT) designated by the ASTM D4742 method. A 1.5 gram test sample of 10W30 engine oil, formulated to meet the SD/CC quality level and containing 0.5% by weight of the test compound, is placed in the test apparatus. The test is then carried out according to the standard procedure and the oxidation induction time, in minutes, is ascertained. A longer induction time indicates a more effective antioxidant stabilizer.

| Test Compound of | Oxidation Induction Time (minutes) |
|---|---|
| Base Oil (no stabilizer) | 113 |
| Example 4 | 138 |

The instant compound provides effective antioxidant protection to the base oil.

What is claimed is:

1. A composition stabilized against the deleterious effects of heat or oxygen which comprises
   (a) a synthetic polymer, and
   (b) an effective stabilizing mount of a compound of formula I, II or III

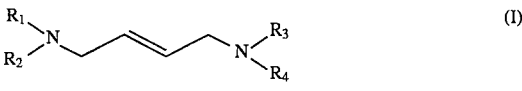

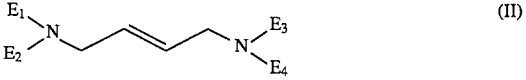

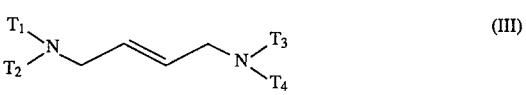

wherein
$R_1$, $R_2$, $R_3$ and $R_4$ are independently a linear or branched alkyl of 8 to 30 carbon atoms; alkyl of 1 to 20 carbon atoms substituted with cycloalkyl of 5 to 12 carbon atoms; or alkyl of 1 to 20 carbon atoms terminated with —OR$_5$, —NR$_6$R$_7$, —SR$_8$, —COOR$_9$ or —CONR$_{10}$R$_{11}$, where $R_5$, $R_6$, $R_7$, $R_8$ and $R_9$ are independently alkyl of 1 to 20 carbon atoms or alkenyl of 3 to 18 carbon atoms, and $R_{10}$ and $R_{11}$ are independently hydrogen or the same meaning as $R_5$; or alkyl of 3 to 18 carbon atoms interrupted by one or more —O—, —S—, —SO—, —SO$_2$—, —CO—, —COO—, —OCO—, —CONR$_{12}$—, —NR$_{12}$CO— or —NR$_{13}$— where $R_{12}$ and $R_{13}$ have the same meaning as $R_{10}$; or $R_1$, R$_2$, R$_3$ and R$_4$ are independently cycloalkyl of 5 to 12 carbon atoms; or alkenyl of 3 to 20 carbon atoms;

E$_1$ is aralkyl of 7 to 15 carbon atoms or said aralkyl substituted on the aryl ring by one to three groups selected from alkyl of 1 to 12 carbon atoms, —CN, —NO$_2$, halogen, —OR$_5$, —NR$_6$R$_7$, —SR$_8$, —COOR$_9$ or —CONR$_{10}$R$_{11}$, where R$_5$, R$_6$, R$_7$, R$_8$, R$_9$, R$_{10}$ and R$_{11}$ are as defined above, E$_2$, E$_3$ and E$_4$ are independently a linear or branched alkyl of 1 to 30 carbon atoms; alkyl of 1 to 20 carbon atoms substituted with cycloalkyl of 5 to 12 carbon atoms; or alkyl of 1 to 20 carbon atoms terminated with —CN, —OR$_5$, —NR$_6$R$_7$, —SR$_8$, —COOR$_9$ or —CONR$_{10}$R$_{11}$, where R$_5$, R$_6$, R$_7$, R$_8$ and R$_9$ are independently alkyl of 1 to 20 carbon atoms or alkenyl of 3 to 18 carbon atoms, and R$_{10}$ and R$_{11}$ are independently hydrogen or the same meaning as R$_5$; or alkyl of 3 to 18 carbon atoms interrupted by one or more —O—, —S—, —SO—, —SO$_2$—, —CO—, —COO—, —OCO—, —CONR$_{12}$—, —NR$_{12}$CO— or —NR$_{13}$— where R$_{12}$ and R$_{13}$ have the same meaning as R$_{10}$; or E$_2$, E$_3$ and E$_4$ are independently cycloalkyl of 5 to 12 carbon atoms, alkenyl of 3 to 20 carbon atoms, aralkyl of 7 to 15 carbon atoms or said aralkyl substituted on the aryl ring by one to three groups selected from alkyl of 1 to 12 carbon atoms, —CN; —NO$_2$, halogen, —OR$_5$, —NR$_6$R$_7$, —SR$_8$, —COOR$_9$ or —CONR$_{10}$R$_{11}$, where R$_5$, R$_6$, R$_7$, R$_8$, R$_9$, R$_{10}$ and R$_{11}$ are as defined above, or aryl of 6 to 10 carbon atoms or said aryl substituted by one to three substituents selected from the group consisting of alkyl of 1 to 20 carbon atoms, cycloalkyl of 5 to 12 carbon atoms and aralkyl of 7 to 15 carbon atoms, and T$_1$, T$_2$, T$_3$ and T$_4$ are independently phenyl or 1-naphthyl.

2. A composition according to claim 1 wherein the synthetic polymer is a polyolefin or an elastomer.

3. A composition according to claim 2 wherein the polyolefin is polypropylene.

4. A composition according to claim 2 wherein the elastomer is crosslinked polypropylene/nitrile rubber.

5. A composition according to claim 1 wherein the compound of component (b) is of formula I where R$_1$, R$_2$, R$_3$ and R$_4$ are independently cycloalkyl of 5 or 6 carbon atoms, a linear or branched alkyl of 8 to 20 carbon atoms or alkyl of 1 to 4 carbon atoms substituted with cycloalkyl of 5 or 6 carbon atoms.

6. A composition according to claim 5 wherein R$_1$, R$_2$, R$_3$ and R$_4$ are the same and are alkyl of 8 to 18 carbon atoms, cyclohexyl or cyclohexylmethyl.

7. A composition according to claim 1 wherein the compound of component (b) is of formula II where E$_1$ is benzyl, benzyl substituted on the phenyl ring by alkyl of 1 to 8 carbon atoms; α-methylbenzyl or 1-naphthylmethyl, and E$_2$, E$_3$ and E$_4$ are independently alkyl of 1 to 20 carbon atoms, benzyl, benzyl substituted on the phenyl ring by alkyl of 1 to 8 carbon atoms or by methoxycarbonyl; α-methylbenzyl; phenyl, 1-naphthyl or said phenyl or said 1-naphthyl substituted by alkyl of 1 to 8 carbon atoms; cyclohexylmethyl or 2-cyanoethyl.

8. A composition according to claim 7 wherein E$_3$ has the same meaning as E$_1$ and is benzyl or 1-naphthylmethyl; and E$_2$ and E$_4$ are alkyl of 1 to 20 carbon atoms, benzyl or 1-naphthylmethyl.

9. A composition according to claim 1 wherein T$_1$ and T$_3$ are phenyl, and T$_2$ and T$_4$ are phenyl or 1-naphthyl.

10. A composition according to claim 9 wherein T$_1$, T$_2$, T$_3$ and T$_4$ are each phenyl.

11. A composition according to claim 1 wherein the compound of component (b) is
N,N,N',N'-tetradecyl-2-butene-1,4-diamine;
N,N,N',N'-tetracyclohexylmethyl-2-butene-1,4-diamine;
N,N,N',N'-tetracyclohexyl-2-butene-1,4-diamine;
N,N,N',N'-tetrabenzyl-2-butene-1,4-diamine;
N,N,N',N'-tetraphenyl-2-butene-1,4-diamine;
N,N'-diphenyl-N,N'-di-1-naphthyl-2-butene-1,4-diamine;
N,N'-dibenzyl-N,N'-di-α-methylbenzyl-2-butene-1,4-diamine;
N,N'-dicyclohexylmethyl-N,N'-dibenzyl-2-butene-1,4-diamine;
N,N'-dibenzyl-N,N'-di-2-cyanoethyl-2-butene-1,4-diamine;
N,N'-di-1-naphthyl-N,N'-dibenzyl-2-butene-1,4-diamine;
N,N-dicyclohexylmethyl-N',N'-dibenzyl-2-butene-1,4-diamine;
N,N,N',N'-tetra-p-methoxycarbonylbenzyl-2-butene-1,4-diamine;
N,N,N',N'-tetra-p-methoxybenzyl-2-butene-1,4-diamine; or
N,N-diphenyl-N',N'-dibenzyl-2-butene-1,4-diamine.

12. A composition stabilized against the deleterious effects of heat or oxygen which comprises
(a) lubricant, and
(b) an effective stabilizing amount of a compound of formula I, or II

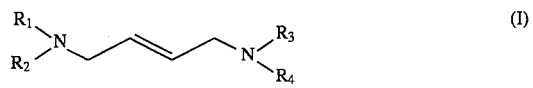

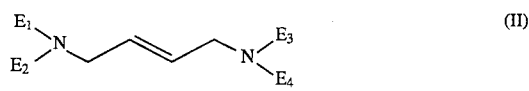

wherein
R$_1$, R$_2$, R$_3$ and R$_4$ are independently a linear or branched alkyl of 8 to 30 carbon atoms; alkyl of 1 to 20 carbon atoms substituted with cycloalkyl of 5 to 12 carbon atoms; or alkyl of 1 to 20 carbon atoms terminated with —OR$_5$, —NR$_6$R$_7$, —SR$_8$, —COOR$_9$ or —CONR$_{10}$R$_{11}$, where R$_5$, R$_6$, R$_7$, R$_8$ and R$_9$ are independently alkyl of 1 to 20 carbon atoms or alkenyl of 3 to 18 carbon atoms, and R$_{10}$ R$_{11}$ are independently hydrogen or the same meaning as R$_5$; or alkyl of 3 to 18 carbon atoms interrupted by one or more —O—, —S—, —SO—, —SO$_2$—, —CO—, —COO—, —OCO—, —CONR$_{12}$—, —NR$_{12}$CO— or —NR$_{13}$— where R$_{12}$ and R$_{13}$ have the same meaning as R$_{10}$; or R$_1$, R$_2$, R$_3$ and R$_4$ are independently cycloalkyl of 5 to 12 carbon atoms; or alkenyl of 3 to 20 carbon atoms;

E$_1$ is aralkyl of 7 to 15 carbon atoms or said aralkyl substituted on the aryl ring by one to three groups selected from alkyl of 1 to 12 carbon atoms, —CN, —NO$_2$, halogen, —OR$_5$, —NR$_6$R$_7$, —SR$_8$, —COOR$_9$ or —CONR$_{10}$R$_{11}$, where R$_5$, R$_6$, R$_7$, R$_8$, R$_9$, R$_{10}$ and R$_{11}$ are as defined above, and E$_2$, E$_3$ E$_4$ are independently a linear or branched alkyl of 1 to 30 carbon atoms; alkyl of 1 to 20 carbon atoms substituted with cycloalkyl of 5 to 12 carbon atoms; or alkyl of 1 to 20 carbon atoms terminated with —CN, —OR$_5$, —NR$_6$R$_7$, —SR$_8$, —COOR$_9$ or —CONR$_{10}$R$_{11}$, where R$_5$, R$_6$, R$_7$, R$_8$ and R$_9$ are independently alkyl of 1 to 20 carbon atoms or alkenyl of 3 to 18 carbon atoms, and R$_{10}$ R$_{11}$ are independently hydrogen or the same meaning as R$_5$;

or alkyl of 3 to 18 carbon atoms interrupted by one or more —O—, —S—, —SO—, —SO$_2$—, —CO—, —COO—, —OCO—, —CONR$_{12}$—, —NR$_{12}$CO— or —NR$_{13}$— where R$_{12}$ and R$_{13}$ have the same meaning as R$_{10}$; or E$_2$, E$_3$ and E$_4$ are independently cycloalkyl of 5 to 12 carbon atoms, alkenyl of 3 to 20 carbon atoms, aralkyl of 7 to 15 carbon atoms or said aralkyl substituted on the aryl ring by one to three groups selected from alkyl of 1 to 12 carbon atoms, —CN, —NO$_2$, halogen, —OR$_5$, —NR$_6$R$_7$, —SR$_8$, —COOR$_9$ or —CONR$_{10}$R$_{11}$, where R$_5$, R$_6$, R$_7$, R$_8$, R$_9$, R$_{10}$ and R$_{11}$ are as defined above, or aryl of 6 to 10 carbon atoms or said aryl substituted by one to three substituents selected from the group consisting of alkyl of 1 to 20 carbon atoms, cycloalkyl of 5 to 12 carbon atoms and aralkyl of 7 to 15 carbon atoms.

13. A composition according to claim 12 wherein the compound of component (b) is of formula I where R$_1$, R$_2$, R$_3$ and R$_4$ are independently cycloalkyl of 5 or 6 carbon atoms, a linear or branched alkyl of 8 to 20 carbon atoms or alkyl of 1 to 4 carbon atoms substituted with cycloalkyl of 5 or 6 carbon atoms.

14. A composition according to claim 13 wherein R$_1$, R$_2$, R$_3$ and R$_4$ are the same and are alkyl of 8 to 18 carbon atoms, cyclohexyl or cyclohexylmethyl.

15. A composition according to claim 12 wherein the compound of component (b) is of formula II where E$_1$ is benzyl, benzyl substituted on the phenyl ring by alkyl of 1 to 8 carbon atoms; α-methylbenzyl or 1-naphthylmethyl, and E$_2$, E$_3$ E$_4$ are independently alkyl of 1 to 20 carbon atoms, benzyl, benzyl substituted on the phenyl ring by alkyl of 1 to 8 carbon atoms or by methoxycarbonyl; α-methylbenzyl; phenyl, 1-naphthyl or said phenyl or said 1-naphthyl substituted by alkyl of 1 to 8 carbon atoms; cyclohexylmethyl or 2-cyanoethyl.

16. A composition according to claim 15 wherein E$_3$ has the same meaning as E$_1$ and is benzyl or 1-naphthylmethyl; and E$_2$ E$_4$ are alkyl of 1 to 20 carbon atoms, benzyl or 1-naphthylmethyl.

17. A composition according to claim 12 wherein the compound of component (b) is
N,N,N',N'-tetradecyl-2-butene-1,4-diamine;
N,N,N',N'-tetracyclohexylmethyl-2-butene-1,4-diamine;
N,N,N',N'-tetracyclohexyl-2-butene-1,4-diamine;
N,N,N',N'-tetrabenzyl-2-butene-1,4-diamine;
N,N'-dibenzyl-N,N'-di-α-methylbenzyl-2-butene-1,4-diamine;
N,N'-dicyclohexylmethyl-N,N'-dibenzyl-2-butene-1,4-diamine;
N,N'-dibenzyl-N,N'-di-2-cyanoethyl-2-butene-1,4-diamine;
N,N'-di-1-naphthyl-N,N'-dibenzyl-2-butene-1,4-diamine;
N,N-dicyclohexylmethyl-N',N'-dibenzyl-2-butene-1,4-diamine;
N,N,N',N'-tetra-p-methoxycarbonylbenzyl-2-butene-1,4-diamine;
N,N,N',N'-tetra-p-methoxybenzyl-2-butene-1,4-diamine; or
N,N-diphenyl-N',N'-dibenzyl-2-butene-1,4-diamine.

* * * * *